United States Patent [19]

Gueremy et al.

[11] Patent Number: 5,240,948
[45] Date of Patent: * Aug. 31, 1993

[54] 3-(3-ALKYLTHIOPROPYL)BENZOTHIAZO-LINE DERIVATIVES, THEIR PREPARATION AND THE MEDICAMENT CONTAINING THEM

[75] Inventors: Claude Gueremy, Houilles; Patrick Jimonet, Villepreux, both of France

[73] Assignee: Rhone-Poulenc Rorer Pharmaceuticals Inc., Collegeville, Pa.

[*] Notice: The portion of the term of this patent subsequent to Apr. 16, 2008 has been disclaimed.

[21] Appl. No.: 647,395

[22] Filed: Jan. 29, 1991

Related U.S. Application Data

[63] Continuation-in-part of Ser. No. 450,231, Dec. 13, 1989.

[30] Foreign Application Priority Data

May 18, 1990 [FR] France .................. 90 06277

[51] Int. Cl.$^5$ ................. C07D 277/82; A61K 31/425
[52] U.S. Cl. ..................................... 514/367; 548/164
[58] Field of Search ........................ 548/164; 514/367

[56] References Cited

U.S. PATENT DOCUMENTS 5,008,280  4/1991  Gueremy ................. 514/367

FOREIGN PATENT DOCUMENTS 375510  6/1990  European Pat. Off. ........... 514/367

OTHER PUBLICATIONS

March, Advanced Organic Chemistry, pp. 360, 361, 1089, 1090 (1985).
Greene, Protective Groups in Organic Synthesis pp. 235, 54.55 (1981).

Primary Examiner—Robert Gerstl
Attorney, Agent, or Firm—Raymond S. Parker, III; Martin F. Savitzky

[57] ABSTRACT

Compounds of formula:

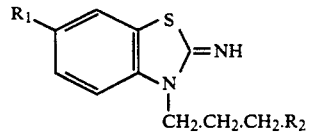

in which $R_1$ represents a polyfluoroalkoxy radical and $R_2$ represents an alkylthio, alkylsulphinyl or alkylsulphonyl radical, their salts, their preparation and the medicaments containing them.

12 Claims, No Drawings

3-(3-ALKYLTHIOPROPYL)BENZOTHIAZOLINE DERIVATIVES, THEIR PREPARATION AND THE MEDICAMENT CONTAINING THEM

This application is a continuation-in-part of U.S. application Ser. No. 450,231, filed Dec. 13, 1989.

BACKGROUND OF THE INVENTION

1. Field of the Invention

This invention relates to 3-(3-alkylthiopropyl)benzothiazoline derivatives which exhibit valuable pharmacological activity against convulsions induced by glutamate and are useful in the prevention and treatment of convulsive phenomena, schizophrenic disorders, and in particular the deficiency forms of schizophrenia, sleep disorders, phenomena linked to cerebral ischemia and neurological conditions in which glutamate through to be implicated, such as Alzheimer's disease, Huntington's chorea, amyotrophic lateral sclerosis and olivopontocerebellar atrophy. Further, the invention relates to medicaments containing said compounds or their salts with pharmaceutically acceptable acids in pure state or in the form of compositions in which they are combined with a pharmaceutically acceptable carrier. The invention also relates to a process for the preparation of said compounds and to the treatment of conditions induced by glutamate.

2. Reported Developments

Glutamate is a nonessential amino acid and the most abundant free amino acid in the central nervous system. It is the putative neurotransmitter of several clinically important pathways, including cortical association fibers, cortifugal pathways and spinal cord pathways. There is substantial evidence implicating the glutamatergic system in certain neurologic diseases associated with olivopontocerebellar atrophy, Huntington's disease, status epilepticus, hypoxia, cerebral ischemia, and hypoglycemia. Accordingly, pharmacologic manipulation of the glutamatergic system appears to have great potential for the prevention and treatment of these neurologic diseases. The prior art has found for example that: glutamate antagonists can prevent the neuronal degeneration associated with ischemia and hypoxia (Simon R. P., Swan J. H. Griffiths T., et al Blockage of N-methyl-D-aspartate receptors may protect against ischemic damage in the brain, Science 1981; 226:850–862 and Rothman S: Synaptic release of excitatory amino acid neurotransmitter mediates anoxic neuronal death, *J. Neurosci* 1984; 4:1884–1891); and glutamate receptor antagonists can be used as potent anticonvulsant agents (Schwarcz R., Meldrum B: Excitatory amino acid antagonists provide a therapeutic approach to neurological disorders, *Lancet* 1985; 2:140–143).

Compounds having certain structural similarity and utility to the compounds of the present invention are disclosed in U.S. Pat. No. 4,918,090.

SUMMARY OF THE INVENTION

The present invention relates to compounds of formula:

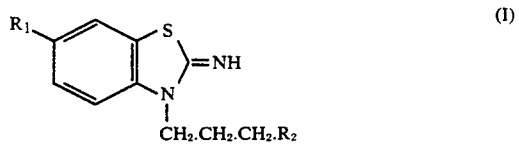

their salts, the processes for their preparation and the medicaments containing them.

In formula (I):
$R_1$ represents a polyfluoroalkoxy radical; and
$R_2$ represents an alkylthio, alkylsulphinyl or alkylsulphonyl radical.

DETAILED DESCRIPTION OF THE INVENTION

In the definitions above and in those which will be given below, the alkyl and alkoxy radicals and the alkyl and alkoxy portions contain 1 to 4 carbon atoms in straight or branched chain.

The polyfluoroalkoxy radicals are preferably trifluoromethoxy, pentafluoroethoxy, 2,2,2-trifluoroethoxy or 1,1,2,2-tetrafluoroethoxy radicals.

The invention also relates to the addition salts of compounds of formula (I) with inorganic or organic acids.

According to the invention, the compounds of formula (I) for which $R_2$ represents an alkylthio radical may be prepared by the action of a derivative of formula:

in which $R_3$ represents an alkyl radical, on a derivative of formula:

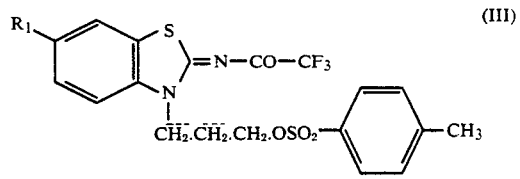

in which $R_1$ has the same meanings as in formula (I).

This reaction generally takes place in an inert organic solvent such as an alcohol (methanol or ethanol for example), at a temperature between 20° C. and the boiling point of the reaction mixture.

The derivatives of formula (III) may be obtained by the action of p-toluenesulphonyl chloride on a derivative of formula:

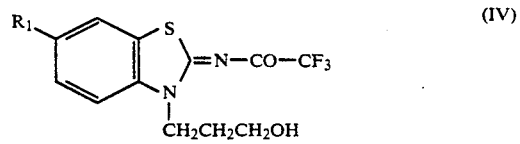

in which $R_1$ has the same meanings as in formula (I).

This reaction preferably takes place in pyridine, at a temperature of between 0° C. and 10° C.

The derivatives of formula (IV) may be obtained by the action of ethyl trifluoroacetate on a derivative of formula:

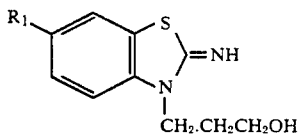

in which R₁ has the same meanings as in formula (I).

This reaction generally takes place in an inert solvent such as an alcohol (methanol or ethanol for example), in the presence of a trialkylamine, at a temperature of close to 20° C.

The derivatives of formula (V) may be obtained by the action of 3-bromopropanol on a derivative of formula:

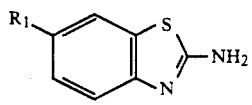

in which R₁ has the same meanings as in formula (I).

This reaction generally takes place in an inert solvent such as an alcohol (ethanol or 2-propanol for example), at boiling point of the solvent.

The derivatives of formula (II) may be obtained by application or adaptation of the method described by L. M. YAGUPOL'SKII et al., Zh, Obshch. Khim., 33(7), 2301-7 (1963) (Chem. Abst., vol 60, 692a-f (1964)).

The compounds of formula (I) for which $R_2$ represents an alkylsulphinyl or alkylsulphonyl radical may be prepared by oxidation of a corresponding derivative of formula (I) for which $R_2$ represents an alkylthio radical, if appropriate followed by a hydrolysis to liberate the imino function.

The oxidation to alkylsulphinyl is generally carried out by means of m-chloroperbenzoic acid, in an inert solvent such as water, dioxane or a mixture of these solvents, at a temperature of close to 20° C.

The oxidation to alkylsulphonyl is generally carried out by means of excess m-chloroperbenzoic acid, in a chlorinated solvent (chloroform or dichloromethane for example), at the boiling point of the solvent.

The hydrolysis is generally effected by means of an acid such as hydrochloric acid, in an inert solvent such as dioxane, at the boiling point of the reaction mixture.

The reaction mixtures obtained by the various processes described above are treated in accordance with conventional physical methods such as evaporation, extraction, distillation, crystallisation, and chromatography or conventional chemical methods such as salt formation.

The compounds of formula (I), in the form of the free base, may optionally be converted to addition salts with an inorganic or organic acid by the action of such an acid in an organic solvent such as an alcohol, a ketone, an ether or a chlorinated solvent.

The compounds of formula (I) and their salts have valuable pharmacological properties. These compounds are active in respect of convulsions induced by glutamate and are therefore useful in the treatment and the prevention of convulsive phenomena, schizophrenic disorders and in particular deficiency forms of schizophrenia, sleep disorders, phenomena associated with cerebral ischemia and neurological complaints where glutamate may be involved, such as Alzheimer's disease, Huntington's chorea, lateral amyotrophic sclerosis and olivopontocerebellar atrophy.

The activity of compounds of formula (I) in respect of convulsions induced by glutamate has been determined using a technique inspired by that of I. P. LAPIN, J. Neural. Transmission, vol. 54, 229–238 (1982); the intracerebroventricular injection of glutamate being effected using a technique inspired by that of R. CHERMAT and P. SIMON, J. Pharmacol. (Paris), vol. 6, 489–492 (1975). Their $ED_{50}$ is generally equal to or less than 10 mg/kg.

The compounds of formula (I) have a low toxicity. Their $LD_{50}$ is higher than 15 mg/kg administered IP to mice.

The following compounds are particularly valuable:
2-imino-3-(3-methylthiopropyl)-6-trifluoromethoxybenzothiazoline;
(RS)-2-imino-3-(3-methylsulphinylpropyl)-6-trifluoromethoxybenzothiazoline; and
2-imino-3-(3-methylsulphonylpropyl)-6-trifluoromethoxybenzothiazoline.

For medicinal use, use may be made of the compounds of formula (I) as such or in the form of salts which are pharmaceutically acceptable, that is to say non-toxic at the doses used.

Examples of pharmaceutically acceptable salts which may be mentioned are the addition salts with inorganic or organic acids, such as acetate, propionate, succinate, benzoate, fumarate, maleate, oxalate, methanesulphonate, isethionate, theophyllineacetate, salicylate, phenolphthalinate, methylene-bis-β-oxynaphthoate, hydrochloride, sulphate, nitrate and phosphate.

The following examples, given without any limitation being implied, show how the invention may be implemented in practice.

EXAMPLE 1

3-(2-Trifluoroacetylimino-6-trifluoromethoxy-3-benzothiazolinyl)propyl p-toluenesulphonate (3.88 g) and sodium methanethiolate (1.03 g) in absolute ethanol (20 cc) are heated at 60° C. for 6 hours. After cooling to a temperature close to 20° C., the reaction mixture is concentrated to dryness under reduced pressure (20 mm Hg; 2.7 kPa). The oily residue is taken up in distilled water (50 cc) and the organic phase is extracted with ethyl ether (50 cc). After drying over magnesium sulphate and concentrating to dryness under reduced pressure, 2-imino-3-(3-methylthiopropyl)-6-trifluoromethoxybenzothiazoline (1.88 g) is obtained, which is converted to the hydrochloride melting at 181° C.

3-(2-Trifluoroacetylimino-6-trifluoromethoxy-3-benzothiazolinyl)propyl p-toluenesulphonate may be prepared by the following process: 3-(2-trifluoroacetylimino-6-trifluoromethoxy-3-benzothiazolinyl)propanol (11 g) is added progressively to p-toluenesulphonyl chloride (10.8 g) in solution in pyridine (200 cc) cooled to 0° C. The reaction is continued for 1 hour at 5° C. and the reaction mixture is then kept cold (6°-7° C.) for 15 hours. After adding distilled water (2 liters), extracting with ethyl acetate (200 cc) washing with 1N hydrochloric acid (2×50 cc), drying over magnesium sulphate and concentrating to dryness under reduced pressure, 3-(2-trifluoroacetylimino-6-trifluoromethoxy-3-benzothiazolinyl)propyl p-toluenesulphonate (6.7 g) melting at 139° C. is obtained.

3-(2-Trifluoroacetylimino-6-trifluoromethoxy-3-benzothiazolinyl)propanol may be prepared in the following way: 3-(2-imino-6-trifluoromethoxy-3-benzothiazolinyl)propanol (24.8 g), ethyl trifluoroacetate (14.2 g) and triethylamine (8.6 g) are stirred in absolute ethanol (250 cc) for 24 hours at a temperature close to 20° C. The reaction mixture is then cooled to 0°–5° C. and the precipitate formed is filtered off and dried. 3-(2-Trifluoroacetylimino-6-trifluoromethoxy-3-benzothiazolinyl)propanol (28.2 g) melting at 144° C. is obtained.

3-(2-Imino-6-trifluoromethoxy-3-benzothiazolinyl)propanol may be prepared by the following process: 2-amino-6-trifluoromethoxybenzothiazole (82 g) and 3-bromopropanol (65 cc) in absolute ethanol (25 cc) are heated for 72 hours at the boil. The mixture is then cooled to a temperature close to 20° C. The oil obtained is taken up in distilled water (1 liter) and the organic phase is extracted with dichloromethane (3×200 cc). After drying over magnesium sulphate and concentrating to dryness under reduced pressure, the crude product is purified by chromatography on a silica column using ethyl acetate as eluent. 3-(2-Imino-6-trifluoromethoxy-3-benzothiazolinyl)propanol (25 g) melting at 106° C. is obtained.

EXAMPLE 2

90% m-chloroperbenzoic acid (2.5 g) is added in the course of about 15 minutes, at a temperature close to 20° C., to 2-imino-3-(3-methylthiopropyl)-6-trifluoromethoxybenzothiazoline (4.2 g) in solution in a mixture (100 cc) of water and dioxane (40/60 by volume). The reaction mixture is stirred at the same temperature for 72 hours. After adding to distilled water (500 cc) and neutralising with 1N sodium hydroxide solution, the reaction mixture is extracted with dichloromethane. After drying over magnesium sulphate and concentrating to dryness under reduced pressure and then purifying by chromatography on a silica column using a mixture of ethyl acetate and methanol (80/20 by volume) as eluent, (RS)-2-imino-3-(3-methylsulphinylpropyl)-6-trifluoromethoxybenzothiazoline (1.2 g) melting at 114° C. is obtained.

EXAMPLE 3

2-(3-Chlorobenzoylimino)-3-(3-methyl-sulphonylpropyl)-6-trifluoromethoxybenzothiazoline (0.7 g) in dioxane (100 cc) is treated with 37% hydrochloric acid (5 cc) for 48 hours at the boil. The reaction mixture is cooled to a temperature close to 20° C. and concentrated to dryness under reduced pressure and the residue is then taken up in distilled water (150 cc). After neutralising with 1N sodium hydroxide solution, extracting with ethyl acetate and forming the oxalate in acetone, 2-imino-3-(3-methylsulphonylpropyl)-6-trifluoromethoxybenzothiazoline (0.2 g) melting at 180° C. is obtained.

2-(3-Chlorobenzoylimino)-3-(3-methyl-sulphonylpropyl)-6-trifluoromethoxybenzothiazoline may be prepared in the following way: 75% m-chloro-perbenzoic acid (5.2 g) is added in the course of about 10 minutes, to 2-imino-3-(3-methylthiopropyl)-6-trifluoromethoxybenzothiazoline (3.9 g) in solution in dichloromethane (100 cc) stirred at a temperature close to 20° C. The reaction mixture is brought to the boil for 18 hours. After cooling to a temperature close to 20° C., the precipitate is filtered off and washed with dichloromethane (50 cc) and the filtrate is concentrated to dryness under reduced pressure after washing with 1N sodium hydroxide solution. The oil obtained is crystallised from ethyl acetate. 2-(3-Chlorobenzoylimino)-3-(3-methylsulphonylpropyl)-6-trifluoromethoxybenzothiazoline (0.6 g) melting at 188° C. is obtained.

The present invention also relates to the medicaments consisting of at least one compound of formula (I) or a salt of such a compound in the pure state or in the form of a composition in which it is combined with any other pharmaceutically compatible product, which may be inert or physiologically active.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transephthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be compressed into tablets, or gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amount employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of required particle size in the case of dispersions and by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal along or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 M/day or from about 0.1 mg to about 50 mg/kg of body weight per day and higher although it may be administered in several different dosage units. Higher dosages are required for oral administration.

In human therapy, the compositions according to the invention are particularly useful in the treatment and the prevention of convulsive phenomena, schizophrenic disorders and in particular deficiency forms of schizophrenia, sleep disorders, phenomena associated with cerebral ischemia and neurological complaints where glutamate may be involved, such as Alzheimer's disease, Huntington's chorea, lateral amyotrophic sclerosis and olivopontocerebellar atrophy.

The following examples illustrate compositions according to the invention:

EXAMPLE A

Using the customary technique, capsules are prepared containing a dose of 50 mg of active compound and having the following composition:

| | |
|---|---|
| 2-imino-3-(3-methylthiopropyl)-6-trifluoro-methoxybenzothiazoline | 50 mg |
| cellulose | 18 mg |
| lactose | 55 mg |
| colloidal silica | 1 mg |
| sodium carboxymethyl starch | 10 mg |
| talc | 10 mg |
| magnesium stearate | 1 mg |

EXAMPLE B

Using the customary technique, tablets are prepared containing a dose of 50 mg of active compound and having the following composition:

| | |
|---|---|
| 2-imino-3-(3-methylsulphinylpropyl)-6-trifluoromethoxybenzothiazoline | 50 mg |
| lactose | 104 mg |
| cellulose | 40 mg |
| polyvidone | 10 mg |
| sodium carboxymethyl starch | 22 mg |
| talc | 10 mg |
| magnesium stearate | 2 mg |
| colloidal silica | 2 mg |
| mixture of hydroxymethylcellulose, glycerol and titanium dioxide (71/3.5/24.5) q.s | 1 complete coated tablet weighing 245 mg |

EXAMPLE C

An injectable solution is prepared containing 10 mg of active compound and having the following composition:

| | |
|---|---|
| 2-imino-3-(3-methylsulphonylpropyl)-6-trifluoro-methoxybenzothiasoline | 10 mg |
| benzoic acid | 80 mg |
| benzyl alcohol | 0.06 cc |
| sodium benzoate | 80 mg |
| 95% ethanol | 0.4 cc |
| sodium hydroxide | 24 mg |
| propylene glycol | 1.6 cc |
| water q.s | 4 cc |

We claim:
1. A compound of the formula:

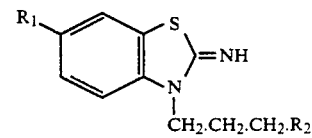

in which R₁ represents a polyfluoroalkoxy radical and R₂ represents an alkylthio, alkylsulphinyl or alkylsulphonyl radical, it being understood that the alkyl and alkoxy portions contain 1 to 4 carbon atoms in a straight or branched chain, as well as its salts with inorganic or organic acids.

2. A compound according to claim 1 for which $R_1$ represents a trifluoromethoxy, pentafluoroethoxy, 2,2,2-trifluoroethoxy or 1,1,2,2-tetrafluoroethoxy radical.

3. A compound according to claim 1 which is 2-imino-3-(3-methylthiopropyl)-6-trifluoromethoxybenzothiazoline.

4. A compound according to claim 1 which is (RS)-2-imino-3-(3-methylsulphinylpropyl)-6-trifluoromethoxybenzothiazoline.

5. A compound according to claim 1 which is 2-imino-3-(3-methylsulphonylpropyl)-6-trifluoromethoxybenzothiazoline.

6. A compound of the formula:

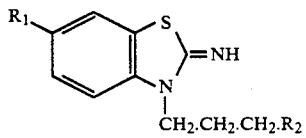

and salts thereof with inorganic or organic acids;
wherein $R_1$ represents a polyfluoroalkoxy radical, and
wherein $R_2$ represents an alkylthio, alkysulphinyl or alkylsulphonyl radical,
wherein said alkyl and alkoxy portions contain 1 to 4 carbon atoms in a straight or branched chain,
wherein the imino group is unsubstituted or substituted with a halogenated acyl group having 1 to 7 carbon atoms.

7. The compound of claim 6 wherein the halogenated acyl group is selected from the group consisting of trifluoroacetyl and 3-chlorobenzoyl.

8. A pharmaceutical composition for the treatment of a medical condition associated with the effects of glutamate which comprises a therapeutically effective amount of a compound of claim 1 in association with a pharmaceutically acceptable carrier.

9. The pharmaceutical composition of claim 6 wherein said compound is selected from the group consisting of:
2-imino-3-(3-methylthiopropyl)-6-trifluoromethoxybenzothiazoline;
(RS)-2-imino-3-(3-methylsulphinylpropyl)-6-trifluoromethoxybenzothiazoline; and
2-imino-3-(3-methylsulphonylpropyl)-6-trifluoromethoxybenzothiazoline.

10. A method for the treatment of a medical condition associated with the effects of glutamate which comprises administering to a subject in need of such treatment an amount of a compound as claimed in claim 1, sufficient to inhibit such effects at least partially.

11. The method of claim 10 wherein said medical condition is convulsion.

12. A method for the treatment of a medical condition associated with the effects of glutamate which comprises administering to a subject in need of such treatment an amount of a composition as claimed in claim 8.

* * * * *